United States Patent [19]

Kershaw

[11] 4,146,555
[45] Mar. 27, 1979

[54] PROCESS FOR PURIFYING ADIPONITRILE

[75] Inventor: Bernard J. Kershaw, Kingston, Canada

[73] Assignee: Du Pont of Canada Limited, Montreal, Canada

[21] Appl. No.: 858,661

[22] Filed: Dec. 8, 1977

Related U.S. Application Data

[63] Continuation-in-part of Ser. No. 717,909, Aug. 26, 1976, abandoned.

[51] Int. Cl.$^2$ .................. C07C 120/08; C07C 121/26
[52] U.S. Cl. ........................ 260/465.8 R; 260/465.2
[58] Field of Search .................. 260/465.8 R, 583 K, 260/583 P, 465.2

[56] References Cited

U.S. PATENT DOCUMENTS

| 3,775,258 | 11/1973 | Kershaw | 260/465.8 R |
| 3,879,436 | 4/1975 | Kersham et al. | 260/465.8 R |

FOREIGN PATENT DOCUMENTS 907059 8/1972 Canada.
912036 10/1972 Canada.
915707 11/1972 Canada.

*Primary Examiner*—Joseph Paul Brust

[57] ABSTRACT

Certain basic impurities, e.g., N-heterocyclic amines such as 2-methyl-4-amino-5,6-trimethylene pyrimidine are removed from adiponitrile by contact with solid acidic sorption agents, e.g., strong acid ion exchange resins before its hydrogenation to hexamethylene diamine to reduce odor and color of products prepared from the diamine.

1 Claim, No Drawings

PROCESS FOR PURIFYING ADIPONITRILE

CROSS-REFERENCE TO RELATED APPLICATIONS

The application is a continuation-in-part of my co-pending application Ser. No. 717,909 filed on Aug. 26, 1976 now abandoned.

BACKGROUND OF THE INVENTION

1. Field of the Invention

The present invention relates to the treatment of adiponitrile and in particular to a process for reducing the amount of basic impurities in crude adiponitrile especially adiponitrile obtained from adipic acid and ammonia.

2. Description of the Prior Art

Adiponitrile obtained from adipic acid contains impurities, some of which boil at temperatures close to the boiling point of adiponitrile. 2-Cyanocyclopentylideneimine, (CPI), is an example of such an impurity. Close boiling impurities frequently cannot be removed efficiently in industrial scale distillation columns and lead to impurities in subsequent derivatives, in particular in hexamethylene diamine, that are difficult to remove. Failure to remove these latter impurities may result in inferior and variable properties, especially in polymers manufactured using such impure hexamethylene diamine. Some techniques for the purification of adiponitrile are known in the art. For example, adiponitrile may be treated with a solid acidic catalyst in the presence of water and at a temperature of at least 140° C. to remove 2-cyanocyclopentylideneimine from the adiponitrile as described in Canadian Pat. No. 912,036 of B. J. Kershaw, issued Oct. 10, 1972.

SUMMARY OF THE INVENTION

A process for reducing the level of N-heterocyclic amines in adiponitrile by contacting said adiponitrile with a solid acidic sorption agent and at a temperature selected from the class consisting of
(1) strong acid cation exchange resins not having a macroreticular structure at 20–100° C.,
(2) strong acid cation exchange resins having a macroreticular structure at 20–110° C., and
(3) molecular sieves at at least 25° C., said process being conducted in the presence of water when molecular sieves comprise said sorption agent.

The adiponitrile so treated can be hydrogenated in the supercritical vapor phase to produce hexamethylene diamine. The hydrogenation is carried out at a temperature within the range 100° to 200° C. under superatmospheric pressures in the presence of ammonia and a catalyst comprising an iron compound in granular form which has been activated by contact with hydrogen at temperatures not exceeding 600° C. The product of the process preferably contains less than 1 part per million of 2-methyl-5,6-trimethylene pyrimidine (MHP).

DETAILED DESCRIPTION OF THE INVENTION

Adiponitrile can be obtained by reacting adipic acid with ammonia in the presence of a dehydrating catalyst, for example, by the techniques disclosed in U.S. Pat. Nos. 2,200,734 and 2,273,633. Such adiponitrile contains impurities which boil at temperatures close to the boiling point of adiponitrile, e.g., 2-cyanocyclopentylideneimine (CPI). These close boiling impurities are not removed efficiently in industrial scale distillation columns and form impurities in subsequent derivatives, e.g., in hexamethylene diamine, that are difficult to remove and result in inferior and variable properties in polymers made from the diamine. Impurities in the form of cyclic amines, especially N-heterocyclic compounds are especially troublesome. Examples of such impurities are 2-methyl-4-amino-5,6-trimethylene pyrimidine (MAP), 2-amino-3,4,5,6-bis (trimethylene) pyridine (ABP), and 2-cyclopentyl-4-amino-5,6-trimethylene pyrimidine (VAP).

When adiponitrile containing the above-discussed impurities is hydrogenated as described by J. R. B. Boocock, F. T. Flood and B. J. Kershaw in Canadian Pat. No. 907,059 which issued on Aug. 8, 1972 and Canadian Pat. No. 915,707 which issued Nov. 28, 1972 to B. J. Kershaw, M. G. Pounder and K. R. Wilkins odoriferous compounds are formed from the N-heterocyclic compounds, especially MAP. There is a need for an improved process for the manufacture of hexamethylene diamine by the hydrogenation of adiponitrile, using iron catalyst, in which the formation of odoriferous compounds is reduced.

It has now been discovered that the above-described impurities can be removed, or at least substantially reduced by contacting the adiponitrile with certain solid acidic sorption agents.

The crude adiponitrile being treated so as to reduce the level of N-heterocyclic amines therein should be essentially free of ammonia which causes less efficient removal of the N-heterocyclic amines and/or decreased capacity of the agent used for the removal of the amines.

The solid acidic sorption agent should be capable of being separated from the adiponitrile after treatment and should not cause deleterious effects in the adiponitrile, for example, by the introduction of significant amounts of impurities, and/or in the hydrogenation of the treated adiponitrile with iron catalyst. The process conditions used in the treatment of the adiponitrile, e.g., temperature, pressure, will depend on the agent with which the adiponitrile is treated, examples of such conditions being discussed hereinafter. In addition, the adiponitrile should be treated under conditions, e.g., of temperature, that prevent significant loss of adiponitrile by, for example, degradation or hydrolysis.

In the first step of the process, adiponitrile is treated with the agent in a continuous process or in a batch process. Preferably, the adiponitrile is continuously passed through a fixed bed of the agent.

While the adiponitrile treated so as to reduce the amount of N-heterocyclic amines therein is described as "crude adiponitrile", the adiponitrile being treated is preferably adiponitrile that has been subjected to partial purification, e.g., by distillation.

The crude adiponitrile may be treated by a variety of techniques in order to reduce the amount of N-heterocyclic amines therein. For example, the crude adiponitrile (substantially free of ammonia) may be treated with a strong-acid cation exchange resin preferably in the presence of water. The adiponitrile should contain at least 1% by weight of water and preferably at least 3% by weight of water. The water content may be as high as 2 parts by weight of water for each part by weight of adiponitrile, this upper limit being determined primarily by practical considerations. The preferred temperature at which the adiponitrile is treated is in the range from 20–100° C.

Alternatively, the crude adiponitrile may be treated in the presence or essentially in the absence of water with a strong-acid cation exchange resin having a macroreticular structure. The preferred temperature at which the adiponitrile is treated is in the range from 20-100° C. Operable resins include the AMBERLYST® 15 synthetic resin catalyst made by Rohm & Haas. The expression "essentially in the absence of water" means the treatment of adiponitrile containing less than 0.1% water.

The amines are removed from the strong-acid cation exchange resin by contacting the resin at ambient temperatures with a strong acid, for example, hydrochloric or sulphuric acid, in excess of the stoichiometric amount of acid required to convert the resin to its acid or hydrogen form. The resin is used in the process of the present invention in its acid or hydrogen form.

Another method for the treatment of adiponitrile uses a molecular sieve selected from the group consisting of Type X and Type Y, and mixtures thereof, in the presence of water. Type Y molecular sieves are preferred. The molecular sieve may be in a polyvalent cation form, the ammonia form or the hydrogen form. It is believed that the relative affinity of the molecular sieve for N-heterocyclic amines over ammonia increases with increasing temperature and that at temperatures of, for example, at least 180° C. the N-heterocyclic amines are preferentially absorbed by the molecular sieve. Thus, the molecular sieves may be used to hydrolyze 2-cyanocyclopentylideneimine, if present, thereby reducing the amount of 2-aminomethyl cyclopentylamine, the hydrogenation product of 2-cyanocyclopentylideneimine, in the hexamethylene diamine subsequently produced from the adiponitrile, as well as reducing the amount of N-heterocyclic amines. Temperatures in the range 180° to 200° C. may be used.

Molecular sieves, which are also referred to as zeolites, are aluminosilicates having a framework structure with cavities capable of being occupied by large ions and water molecules. Molecular sieves may be used as catalysts, as ion exchange materials or as absorbent materials. There are many types of molecular sieves and their properties depend on, for example, the framework structure of the aluminosilicate and the resultant pore size, the silica/alumina ratio and the type of cation in the structure. Examples of molecular sieves of relatively large pore size are Types X and Y, both of which are structurally related to the mineral faujasite, $(Na_2, Ca, Mg)_{60} (AlO_2)_{60}(SiO_2)_{132} \cdot 260H_2O$. Type Y has a higher silica/alumina ratio than Type X. Type X molecular sieves have been disclosed in U.S. Pat. No. 2,882,244 of R. M. Milton which issued Apr. 14, 1959 and Type Y molecular sieves have been disclosed in U.S. Pat. No. 3,130,007 of D. W. Breck which issued Apr. 21, 1964. The basic crystal structures of Type X and Type Y molecular sieves may be identified by X-ray diffraction. Type X and Type Y molecular sieves are available in many forms, e.g., with univalent cations, for example, sodium, ammonia, hydrogen and with multivalent cations, for example, calcium, magnesium, nickel. As is disclosed in the aforementioned U.S. Pat. No. 3,310,007 molecular sieves are generally synthesized in the sodium form and other types are derived therefrom. Molecular sieves are discussed in greater detail in "Molecular Sieve Zeolites: Trendsetters in Heterogeneous Catalysis" by P. E. Pickert et al. in Chemical Engineering, July 29, 1968, pages 2-11 and in bulletins on LINDE® molecular sieves obtainable from the Linde Division of Union Carbide Corporation, for example, bulletins entitled "A Report on Molecular Sieve Catalysts" and "A Report on Molecular Sieve Catalyst SK-500".

A number of techniques for regeneration of molecular sieves may be used. For example, the molecular sieve may be treated with a solution of ammonia at temperatures of from ambient to about 70° C. followed by a heat treatment of the molecular sieve to remove ammonia. Alternatively the molecular sieve may be heated under an inert gas, treated with steam at high temperatures or treated with a base of higher affinity for the molecular sieve that the amines followed by treatment to remove the base.

The pressure used in the treatment of the adiponitrile to remove the amines is not critical. The pressure will depend primarily on other process variables, for example, the temperature at which the treatment process is operated.

After treatment to reduce the level of N-heterocyclic amines therein the adiponitrile is hydrogenated in the super-critical vapor phase to produce hexamethylene diamine. The hydrogenation is carried out at temperatures in the range 100° C. to 200° C. under a superatmospheric pressures in the presence of ammonia and a catalyst. The catalyst comprises an iron compound in granular form which has been activated by contact with hydrogen at temperatures not exceeding 600° C.; the iron compound being capable ultimately of conversion into elemental iron. By "super-critical vapor phase" is meant a condition in which the temperature of the reactor is above the pseudo-critical temperature of the reactor feed mixture.

When the iron catalyst is used in a fixed bed it is preferably used in relatively coarse granular form, e.g., a particle size of from about 0.25 to 0.50 cm. Much finer particle sizes tending to powders may be used in a fluid bed or in a slurry-type reactor.

The preferred method of activation of the iron catalyst is to treat iron oxide by heating it at about 400° C. in a furnace under a stream of dry hydrogen for 40 to 50 hours using a relatively high flow rate for the stream of hydrogen. If activation is allowed to proceed for too long a period, sintering of the catalyst may occur. It is desirable that substantially no water be present during the activation treatment. The catalyst prepared in this manner will frequently show surface areas of up to 30-35 m$^2$/g. The activation of iron catalysts is described in greater detail in the aforementioned Canadian Pat. No. 907,059 of Boocock et al.

The hydrogenation step of the process of the present invention is particularly adapted for continuous operation. The temperature of the hydrogenation should be regulated within the range of from 100° C. 200° and accurately maintained during the continuous reaction by conventional procedures such as the regulation of flow rates and the temperature of the reactants. Temperatures of 105° C. to 165° C. especially 110° C. to 150° C. are preferred. The hexamethylene diamine formed on hydrogenation of adiponitrile should contain less than 1 ppm of MHP.

The following examples are presented to illustrate, but not to restrict the present invention.

EXAMPLE I

A sample of 100 ml of crude adiponitrile, obtained from adipic acid and ammonia and hereinafter referred to as adiponitrile #1, was heated to 100° C. 1 g of AM- BERLYST ® 15 cation exchange resin, a strong-acid cation exchange resin of macroreticular structure, was added to the adiponitrile and the mixture was stirred for 2 hours at 100° C. The cation exchange resin was filtered off and the filtrate of purified adiponitrile, referred to hereinafter as adiponitrile #2, was analyzed using gas chromatographic techniques.

The results of the analysis are given in Table I.

EXAMPLE II

A sample of 100 ml of adiponitrile #1 was mixed with 6 ml of water and 1 g of DOWEX ® 50W-X8, a strong-acid cation exchange resin obtainable from the Dow Chemical Company. The mixture was stirred for one hour at ambient temperature and then filtered. The filtrate of adiponitrile was partially dehydrated by heating to 160° C. under reduced pressure (12 mm Hg). The dehydrated adiponitrile, hereinafter referred to as adiponitrile#3, was analyzed using gas chromatographic techniques.

The results of the analysis are given in Table I.

Approximately 28 g of −8+14 mesh sample of a naturally occurring iron oxide ($Fe_2O_3$) containing a few percent of silica and other trace impurities was activated by heating in a stream of hydrogen (16 l/hr.) and nitrogen (2.5 l/hr.) at a temperature of 300–350° C. until essentially all of the iron oxide has been converted to elemental iron.

2 g of adiponitrile, 1 g of the activated iron catalyst and 20 g of anhydrous ammonia were added to a stainless steel autoclave having a capacity of 100 ml. The autoclave was then pressurized to about 90 kg/cm$^2$ with hydrogen. The autoclave was then heated to 180° C. and maintained at 180° C. for 30 minutes. The autoclave was continuously agitated during this period at elevated temperature. After cooling the product obtained was dissolved in a minimum amount of water and analyzed for MHP using gas chromatographic techniques. Further experimental details and the results obtained are given in Table II.

Adiponitrile #1, ammonia and hydrogen were fed to a continuous reactor that was 2.5 cm in diameter and 35 cm in length and which contain an activated fused iron oxide containing 3% of alumina. The hexamethylene diamine obtained was analyzed using gas chromatographic techniques. Further experimental details and the results obtained are given in Table III.

As a comparison the iron catalyst was replaced with a cobalt catalyst of the type described as cobalt catalyst (X) in Canadian Pat. No. 915,707. Experimental details and the results obtained are given in Table III.

The results show that under similar conditions the hydrogenation of adiponitrile using an iron catalyst results in the formation of the odorous compound MHP whereas with a cobalt catalyst MHP is not formed.

TABLE I

| Adiponitrile (#) | 1 | 2 | 3 |
|---|---|---|---|
| Impurities (%) | | | |
| CPI | 0.175 | 0.043 | 0.109 |
| Succinimide | 0.080 | 0.073 | 0.083 |
| MAP | 0.026 | 0.000 | 0.000 |
| ABP | 0.104 | 0.0075 | 0.0010 |
| CVA | 0.092 | 0.134 | 0.096 |
| VAP | 0.0076 | 0.000 | 0.000 |
| Water | 0.060 | 0.080 | 0.020 |

N.B. all analyses expressed as percentages on a weight volume basis, remaining component essentially adiponitrile.

TABLE II

| Run No. | 1 | 2 | 3 | 4 | 5 |
|---|---|---|---|---|---|
| Adiponitrile # | 1 | 1 | 1 | 2 | 4 |
| Autoclave Pressure (kg/cm$^2$) | 224 | 249 | 214 | 226 | 229 |
| MHP (%) | 0.0011 | 0.0011 | 0.0010 | 0.0000 | 0.0000 |
| Odor | yes | yes | yes | no | no |

TABLE III

| Run No. | 1 | 2 | 3 | 4 |
|---|---|---|---|---|
| Catalyst | Fe | Fe | Co | Co |
| Adiponitrile (g/hr.) | 399 | 470 | 488 | 484 |
| Ammonia (g/hr.) | 1780 | 2200 | 1800 | 2080 |
| Hydrogen (l/min.) | 27.4 | 39.2 | 36.8 | 37.8 |
| Reactor Temperature (° C) | | | | |
| Inlet | 110 | 104 | 88 | 95 |
| Outlet | 155 | 144 | 132 | 136 |
| Hexamethylene Diamine, yield (%) | 97.0 | 97.8 | 96.8 | 96.6 |
| MHP in Hexamethylene Diamine (%) | 0.0019 | 0.0011 | 0.000 | 0.000 |

Note: Adiponitrile # 1 had not been treated so as to reduce the amount of N-heterocyclic amines therein.

EXAMPLE III

To 50 ml of a crude adiponitrile having the following composition:

| | |
|---|---|
| 2-cyanocyclopentylideneimine (CPI) | 0.15% |
| 2-methyl-4-amino-5,6-trimethylene pyrimidine (MAP) | 0.028% |
| 2-amino-3,4,5,6-bis (Trimethylene) pyridine (ABP) | 0.062% |
| Acyanovaleramide | 0.13% |
| water | 0.1% | were added 0.5 g of AMBERLYST ® 15 cation exchange resin. The resultant mixture was stirred for 20 minutes at ambient temperature and then analyzed by gas chromatography. The results were as follows:

| | Impurity Levels in Adiponitrile* | | |
|---|---|---|---|
| Time | CPI | MAP | ABP |
| 0 min. | 0.15 | 0.028 | 0.062 |
| 20 min. | 0.15 | 0.020 | 0.045 |

*in % weight/volume.

EXAMPLE IV

The procedure of Example III was repeated at a temperature of 100° C. The results were as follows:

| | Impurity Levels in Adiponitrile | | |
|---|---|---|---|
| Time | CPI | MAP | ABP |
| 0 min. | 0.15 | 0.028 | 0.062 |
| 15 min. | 0.12 | 0.013 | 0.027 |
| 35 min. | 0.080 | 0.003 | 0.000 |

EXAMPLE V

To demonstrate the effect of process variables the procedure of Example III was repeated at different temperatures and resin contents. The results were as follows:

| Run No. | 1 | 2 | 3 | 4 |
|---|---|---|---|---|
| Temperature (° C) | 104 | 104 | 58 | 58 |

-continued

| Resin (% by weight) | | 1.0 | 0.5 | 1.0 | 0.5 |
|---|---|---|---|---|---|
| Impurity Levels | | | | | |
| (i) CPI | 0 minutes | 0.15 | 0.15 | 0.15 | 0.15 |
| | 15 minutes | 0.097 | 0.13 | 0.13 | 0.15 |
| | 30 minutes | 0.084 | 0.12 | 0.12 | 0.15 |
| | 60 minutes | 0.073 | 0.11 | 0.090 | 0.14 |
| (ii) MAP | 0 minutes | 0.028 | 0.028 | 0.028 | 0.028 |
| | 15 minutes | 0.011 | 0.017 | 0.013 | 0.020 |
| | 30 minutes | 0.005 | 0.016 | 0.005 | 0.020 |
| | 60 minutes | 0.001 | 0.013 | 0.008 | 0.019 |
| (iii) ABP | 0 minutes | 0.062 | 0.062 | 0.062 | 0.062 |
| | 15 minutes | 0.019 | 0.035 | 0.036 | 0.044 |
| | 30 minutes | NA | 0.030 | 0.032 | 0.041 |
| | 60 minutes | 0.020 | 0.024 | 0.015 | 0.040 |

NA — not available

EXAMPLE VI

In the runs of this example, and in Example VII hereinafter, three different samples of adiponitrile were used. The compositions of the adiponitrile are given in Table IV.

With reference to the runs in Table V, adiponitrile was mixed with water and molecular sieve powder in the quantities specified. The mixture was stirred for the time specified. The molecular sieve used in all runs was a Type Y molecular sieve in the polyvalent cation form obtained from the Linde Division of Union Carbide Corporation (SK-500®). The molecular sieve was filtered off before analysis. Details of the runs the results obtained are given in Table V.

EXAMPLE VII

Using the procedure of Example VI adiponitrile was treated with a Type Y molecular sieve in the ammonia form obtained from the Linde Division of Union Carbide Corporation (SK-41®). Details of the runs and the results obtained are given in TABLE VI.

EXAMPLE VIII

To show that the organic amines may be displaced from the molecular sieve, 10 ml of adiponitrile #4 was mixed with 1 g of SK-500® (polyvalent cation form) and 1 ml of water. The mixture was stirred for 20 minutes at room temperature and then the sieve was filtered off. The sieve so obtained was extracted with aqueous ammonia using a soxhlet extraction apparatus.

The results were as follows:

| Component | Removal from Adiponitrile (%) | Recovery from Molecular Sieve (%) |
|---|---|---|
| MAP | 91 | 83 |
| VAP | 93 | 85 |

To show that the molecular sieve may be regenerated, 50 ml of adiponitrile #5 was mixed with 3 ml water and 0.5 g of SK-500® molecular sieve (polyvalent cation form) and stirred for 30 minutes at room temperature. The sieve was filtered off and the amines were displaced therefrom by the method of Example VII. The filtrate (filtrate #1) was analyzed. The sieve was then dried at 90° C. for 4 hours and following which it was mixed with 50 ml of adiponitrile #5 and 3 ml of water. This mixture was stirred for 2 hours at room temperature. The sieve was filtered off and the filtrate (filtrate #2) analyzed.

The results were as follows:

| Filtrate | Removal of Amines MAP | (%) * ABP |
|---|---|---|
| #1 | 58 | 57 |
| #2 | 19 | 17 |

* Removal of amines on weight percent basis from the adiponitrile as indicated by analysis of filtrate.

| Filtrate | Removal of Amines MAP | (%) * ABP |
|---|---|---|
| #1 | 58 | 57 |
| #2 | 19 | 17 |

* Removal of amines on weight percent basis from the adiponitrile as indicated by analysis of filtrate.

To show regeneration of the molecular sieve at a higher temperature, 200 ml of adiponitrile #4 was mixed with 12 ml of water and 2 g of SK-500® molecular sieve (polyvalent cation form) and stirred for 45 minutes at room temperature. The molecular sieve was filtered off and the filtrate (filtrate #1) was analyzed. The molecular sieve was treated with aqueous ammonia and then heated at 260° C. under a flow of nitrogen for about 12 hours. 0.8 g of the molecular sieve so obtained was mixed with 40 ml of adiponitrile #4 and 2.4 ml of water and stirred for 15 minutes. The molecular sieve was filtered off and the filtrate (filtrate #2) was analyzed.

The results were as follows:

| Filtrate | Removal of Amines MAP | (%) ABP |
|---|---|---|
| #1 | 70 | 65 |
| #2 | 82 | 82 |

EXAMPLE IX

To 50 ml of a crude adiponitrile containing approximately 420 ppm of MAP and 750 ppm of ABP were added 3 ml of water and 1 g of SK-500® molecular sieve. The mixture was stirred for 16 minutes at room temperature, filtered and the adiponitrile was analyzed. The MAP and ABP in the adiponitrile had been reduced by 85% and 96% respectively.

The procedure was repeated using Silica Alumina 979, an amorphous silica alumina obtained from W. R. Grace. Approximately 17% of the MAP was removed from the adiponitrile.

TABLE IV*

| Component | Adiponitrile #4 | Adiponitrile #5 | Adiponitrile #6 |
|---|---|---|---|
| MAP | 0.042 | 0.042 | 0.03 |
| ABP | 0.075 | 0.075 | 0.07 |
| VAP | 0.075 | 0.075 | — |
| CPI | 0.35 | 0.38 | 0.12 |
| Δcyanovaleric acid | 1.0 | ca 0.0 | ca 0.0 |
| Δcyanovaleramide | 0.5 | 0.3 | ca 0.2 |
| adipimide | 0.6 | ca 0.0 | — |

*all analyses expressed as percentages on a weight/volume basis, remaining component essentially adiponitrile.

TABLE V

| Run No. | 1 | 2 | 3 | 4 |
|---|---|---|---|---|
| Reaction Mixture | | | | |
| Adiponitrile (ml) | 50 | 50 | 100 | — |
| type | #4 | #5 | #6 | — |
| Water (ml) | 3 | 3 | 1 | — |

TABLE V-continued

| Run No. | | 1 | 2 | 3 | 4 |
|---|---|---|---|---|---|
| Molecular Sieve (g) | | 1 | 1 | 1 | — |
| Reaction Conditions | | | | | |
| Temperature (° C) | | ambient | ambient | 103 | 178 |
| Time (min) | | 30 | 30 | 30 | 15 |
| Analysis | | | | | |
| MAP before | | 0.042 | 0.042 | 0.03 | 0.006 |
| | after | 0.020 | 0.006 | 0.006 | 0.007 |
| ABP before | | 0.075 | 0.075 | 0.07 | 0.006 |
| | after | NA* | 0.003 | 0.006 | 0.006 |
| CPI before | | 0.035 | 0.038 | 0.12 | 0.10 |
| | after | NA | NA | 0.10 | 0.07 |

*NA - not available
** Run 4 was made as follows: at the completion of Run 3, a sample was taken for analysis and the remainder of the reaction mixture was treated according to the conditions specified in Run 4. The treated material in Runs 3 and 4 was of lighter color than the adiponitrile before treatment.

TABLE VI

| Run No. | | × 5 | 6* |
|---|---|---|---|
| Reaction Mixture | | | |
| Adiponitrile (ml) | | 100 | — |
| | type | 6 | — |
| Water (ml) | | 1 | — |
| Molecular Sieve (g) | | 1 | — |
| Reaction Conditions | | | |
| Temperature (° C) | | 104 | 173 |
| Time (min) | | 30 | 15 |
| Analysis | | | |
| MAP before | | 0.03 | 0.02 |
| | after | 0.02 | 0.002 |
| ABP before | | 0.07 | 0.05 |
| | after | 0.05 | 0.01 |
| CPI before | | 0.12 | 0.11 |
| | after | 0.11 | 0.02 |

*Run 6 relates to Run 5 in the same way as Run 4 relates to Run 3.

I claim:

1. A process for substantially reducing the level of N-heterocyclic amines in adiponitrile made from adipic acid and ammonia by contacting said adiponitrile essentially free of ammonia with a solid acidic sorption agent and at a temperature selected from the class consisting of
   (1) strong acid cation exchange resins not having a macroreticular structure at 20–100° C.,
   (2) strong acid cation exchange resins having a macroreticular structure at 20–110° C., and
   (3) molecular sieves selected from the group consisting of Type X, Type Y, and mixtures thereof at a temperature in the range 25° C. –104° C. said process being conducted in the presence of at least 0.1% by weight of water when molecular sieves comprise said sorption agent.

* * * * *